United States Patent
Nordberg et al.

(10) Patent No.: US 10,156,523 B2
(45) Date of Patent: Dec. 18, 2018

(54) OPTICAL MEASURING SYSTEM BASED ON RAMAN SCATTERING

(71) Applicant: TOTALFOERSVARETS FORSKNINGSINSTITUT, Stockholm (SE)

(72) Inventors: Markus Nordberg, Umea (SE); Henric Oestmark, Hoeloe (SE)

(73) Assignee: TOTALFOERSVARETS FORSKNINGSINSTITUT, Stockholm (SE)

( * ) Notice: Subject to any disclaimer, the term of this patent is extended or adjusted under 35 U.S.C. 154(b) by 0 days.

(21) Appl. No.: 15/747,203

(22) PCT Filed: Jul. 6, 2016

(86) PCT No.: PCT/SE2016/000038
§ 371 (c)(1),
(2) Date: Jan. 24, 2018

(87) PCT Pub. No.: WO2017/018936
PCT Pub. Date: Feb. 2, 2017

(65) Prior Publication Data
US 2018/0217066 A1 Aug. 2, 2018

(30) Foreign Application Priority Data

Jul. 24, 2015 (SE) .................... 1500317-1

(51) Int. Cl.
*G01J 3/44* (2006.01)
*G01N 21/65* (2006.01)
*G01N 33/22* (2006.01)
*G01J 3/02* (2006.01)

(52) U.S. Cl.
CPC ............ *G01N 21/65* (2013.01); *G01J 3/0208* (2013.01); *G01J 3/0229* (2013.01); *G01J 3/44* (2013.01); *G01N 33/227* (2013.01); *G01N 2201/06113* (2013.01)

(58) Field of Classification Search
CPC ........ G01N 21/65; G01N 21/64; G01N 33/22; G01N 21/47; G01J 3/02; G01J 3/44; G01J 3/28; G01J 3/00
See application file for complete search history.

(56) References Cited

U.S. PATENT DOCUMENTS

| | | | |
|---|---|---|---|
| 2007/0263914 A1* | 11/2007 | Tibbetts | G01J 3/02 382/129 |
| 2008/0174777 A1 | 7/2008 | Carron | |
| 2009/0040516 A1 | 2/2009 | Fritz | |
| 2014/0052386 A1 | 2/2014 | Guenther | |

OTHER PUBLICATIONS

Galvis-Carreno et al. Efficient reconstruction of Rama imaging based on compressive sensing. In: DYNA 81 (188), pp. 116-124, Dec. 2014.

* cited by examiner

*Primary Examiner* — Abdullahi Nur
(74) *Attorney, Agent, or Firm* — Jacobson Holman, PLLC

(57) ABSTRACT

A stand-off optical measuring system based on Raman scattering for detecting and identifying chemical threat substances includes a spectrometer having a dispersive device in front of a 2-dimensional detector, with the entrance of the spectrometer being a coded aperture. The measuring system is configured to be able to quickly adapt to different measuring conditions by the coded aperture being a programmable coded aperture.

3 Claims, 2 Drawing Sheets

OPTICAL MEASURING SYSTEM BASED ON RAMAN SCATTERING

BACKGROUND OF THE INVENTION

1. Field of the Invention

The present invention relates to an optical measuring system based on Raman scattering. It is a stand-off system for detecting and identifying chemical threat substances, which systems can be optimized for different scenarios.

2. Description of Related Art

During the last decades several terrorist attacks have been carried out, almost all with different types of IED:s (Improvised Explosive Device). Some have been placed in boxes, other in bottles or vehicles. This makes it very difficult to know what to look for when searching for IED:s. One common thing for all IED:s are, however, that they contain some kind of explosive material. The explosive itself is rarely visible from the outside; traces of the explosive can nevertheless almost always be found outside the IED in form of particles or molecules in the air surrounding it.

It is not trivial to detect and identify these traces. Developments during the last years of smaller pulsed lasers and high sensitive detectors have shown, however, stand-off optical methods such as Raman, fluorescence and infrared spectroscopy to be promising and usable techniques. Unfortunately no existing method can be used for all cases due to the different forms of the explosive material to be detected and identified, such as vapour, particles, liquid and bulk. It has so far been necessary to use a specialized instrument for each case.

One of the main limitations of existing detectors is that they can only record two dimensions (2-d), at the same time. As an example, one dimension can be spatial and one dimension spectral. Such equipment can be used to detect explosives in a number of cases where two spatial dimensions are not important. They have a problem, however, in finding small particles, where two spatial dimensions are vital in order to be able to distinguish between the spectrum from a particle and the background surface.

For a "non-moving" object can done by either a) scanning the spatial dimensions and record the full spectrum from each point on the surface or b) use a tunable filter and thereby collect two spatial dimensions and scan the spectrum. Both of these techniques have their own area of use, but both of these techniques are time consuming. A demand on a new measuring system is that one and the same system should able to cover every different measuring scenario, and in order to be able to do so it must have the possibility to record the two spatial dimensions as well as the spectral dimension at the same time Below follows examples of scenarios that demands different measuring equipment.

In a first scenario, the Police receive an alarm of a suspicious bomb and arrive on the scene. Initially, high precaution must be taken and the examination must start from a long distance. This is more or less only possible if there are large quantities of the unknown substance visible, e.g. if it is in a transparent bottle or container. The air above the substance could also be examined by resonant Raman spectroscopy (RRS) to detect explosive vapour from a bomb. In both of these cases point detection can be used.

If nothing is found, the Police may move closer to the object to be able to find traces of explosives outside e.g. in fingerprints. In this case, very sensitive techniques such as 2-d spectral imaging must be used. If nothing is detected still and the container is semi-opaque, e.g. of plastic, it is possible to use spatial offset Raman spectroscopy (SORS) to measure through the container.

In a second scenario, a suspicious car outside a building is reported. The Police that arrive on the scene may start by using imaging Raman spectroscopy from outside the car in search for explosive particles e.g. at the door, seat belts, steering wheel or the trunk, where traces are most likely to exist. If it is possible to measure into the car it is also possible to examine bulk substances using point detection. Any semi-opaque container might be examined by using SORS.

In a third scenario, a military troop has found a possible roadside bomb. First the air above the possible bomb may be scanned using point detection. If nothing is found, the object itself and the ground around it can be scanned using imaging techniques to find explosive particles. Again, if the container is made of a semi-opaque material, the object can be scanned using SORS to identify the substance inside.

As has been exemplified, there are a number of known, different types equipment using Raman spectroscopy that are each suitable for certain specific measuring conditions. There exists, however, no measuring equipment that can be used for many, and absolutely not for all, measuring modes, and especially not one that is able to be reconfigured rapidly for different measuring modes.

One way of categorizing different measuring modes are:
1. 0-dimensional; point measurement
   a. Bulk detection; measurement at larger quantities and at larger maximum distances <500 m
   b. Gas phase detection; measurements on the air above a suspicions object, Resonant Raman Spectroscopy (RRS)
   c. Detection of smaller objects at well-defined locations
2. 1-dimensional; line measurement
   a. Bottle detection; measurement through semi-opaque containers, Spatial Offset Raman Spectroscopy (SORS)
   b. Surface detection; measurement on flat surfaces with object in well-defined locations, scanning
   c. Particle detection; trace measurement from e.g. fingerprints, scanning
3. 2-dimensional; surface measurement
   a. Particle detection; trace measurement from e.g. fingerprints, imaging
   b. Bottle detection; measurement through semi-opaque containers, imaging or Spatial Offset Raman Spectroscopy (SORS)

SUMMARY OF THE INVENTION

The present invention relates to an optical measuring system based on Raman scattering that overcomes the previous need for different measuring equipment for different measuring circumstances. This is achieved by the invention comprising a device that can be configured for many different detection modes, by being designed in the way that is evident from the following independent claim. The other claims define suitable embodiments of the invention.

BRIEF DESCRIPTION OF THE DRAWINGS

The invention will in the following be described with reference to the accompanying drawings, in which.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

As a starting-point for a description of a measuring device according to the invention that is able to be used in many applications and embodiments, in the following different prior art systems for Raman spectroscopy are first described in some detail. It will also be evident how parts of these can be combined to reach the object of the invention.

The systems include a pulsed laser and a gated detector e.g. an ICCD-camera, in order to efficiently suppress the ambiance light. The laser is not shown in the figures. Different commonly used laser wavelengths could be used. In an embodiment of the invention the wavelengths are the second, third and fourth harmonics of the YAG-laser (532 nm, 355 nm and 266 nm respectively), but also wavelengths below 250 nm can be used to naturally suppress the fluorescence from the target. UV-wavelengths are preferred from an eye-safe perspective, but demands more expensive optics in order to retain high transmission in the system. All systems include a spectrometer comprising a dispersive element followed by a 2-d detector. Here and in the following, a dispersive element means a chromatic dispersive element.

Bulk or Gas Phase Detection

Figure 1:
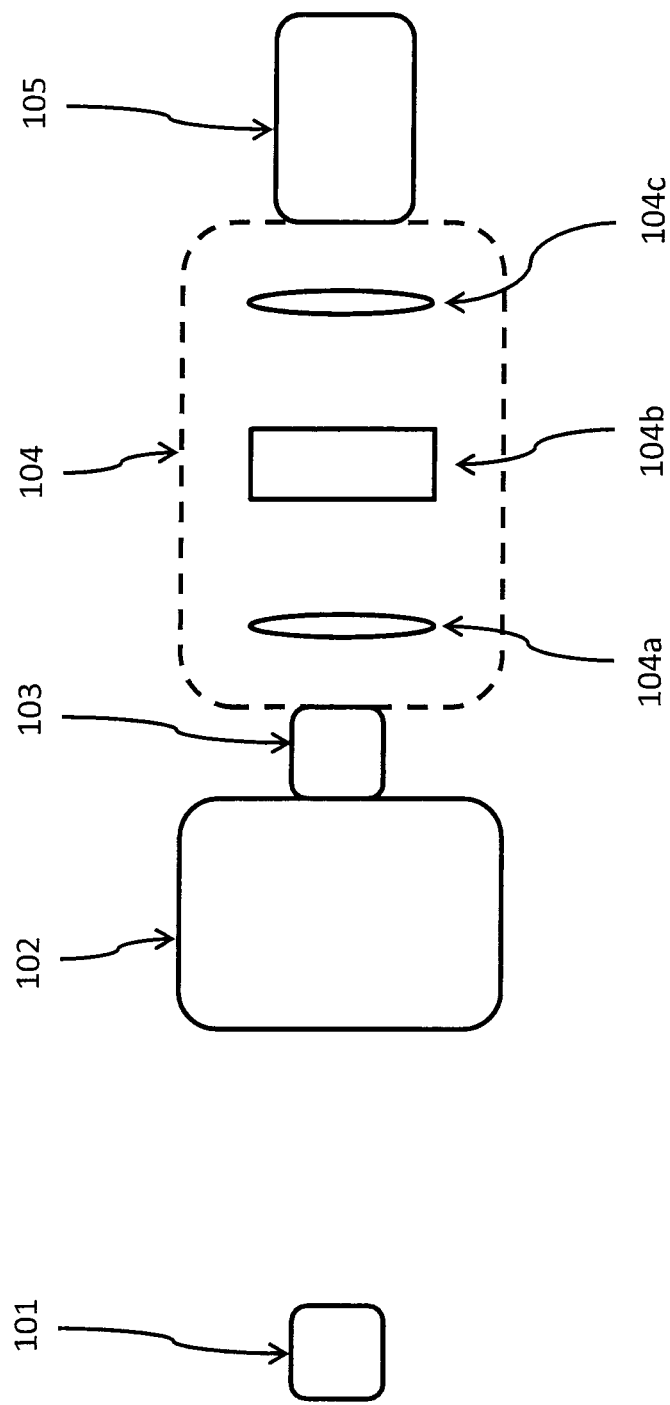
FIG. 1 shows a schematic drawing over a measuring system designed to detect Raman scattered photons.

FIG. 1 shows a schematic drawing over a prior art system designed to detect Raman scattered photons from bulk quantities of an unknown material. From left to right it shows a target 101, collection imaging optics 102, a round to slit optical fibre 103, a dispersive device 104 followed by a 2-d detector 105. The dispersive device comprises a first imaging lens 104a and a second imaging lens 104c on either side of a dispersive element 104b, which latter could e.g. be a grating. The slit side of the optical fibre works as the entrance slit to the dispersive device.

This system can be optimized for high spectral resolution while the spatial resolution is limited to the number of fibres, typical <50. Because of this, the system is limited to bulk amounts or gas phase detection. It can be used, however, up to a distance of several hundreds of meters.

If a laser with a short wavelength, typical <300 nm, is used, the system can gain from resonant Raman effects from the target and the Raman signal is significant enhanced, making it possible to detect molecules in gas phase above or in the vicinity of the target.

A large drawback with a system that uses optical fibres is that when the collected light has very short wavelengths, as in the case of resonant Raman spectroscopy (RRS), the optical transmission in the fibre drops significantly.

Detection in Semi-Opaque Bottles

A general layout of a system for Raman spectroscopy is shown in FIG. 1. To detect Raman scattered photons from unknown material inside a bottle or container made of semi-opaque material, such as plastic, you can use Spatial Offset Raman Spectroscopy (SORS). In the general layout of the system according to FIG. 1, the optical fibre is exchanged for an ordinary slit of a spectrometer. The entrance slit 103 of the spectrometer is imaged on the target area 101 and a laser beam is focused in the middle of the line on the target.

Materials inside the bottle will Raman scatter the laser light, which will reach the surface of the target through random walk. Different depths will end up at different distances from the laser spot and form a circle having the same properties, provided the surface is flat. If the surface is curved, as in a bottle side, they will form an ellipse. The slit 103 will transect the circles or ellipses so that different scattering depth will be imaged onto different positions on the slit of the spectrometer. The system can therefore resolve the spectrum at different depth at the same time, i.e. one spectral dimension (by means of the dispersive element) and one spatial dimension (the depth) are collected on a 2-d detector.

Detection of Single Particles

When detecting very small single particles in the order of 100 μm, most techniques experience problems from the influence of the background, since the area of the particle is a small fraction of the whole collection area. This means that the signal from a small particle vanishes in the much larger signal from the background or, if the collection area is reduced to be small enough for the system to be able to detect the signal from a particle, it will take too long time to scan a large target, such as the trunk of a car.

To overcome this, it is possible to use an imaging detection system instead. In such a system each point or small sub-area of the collecting area is imaged onto the detector. The interference from any other part of the collection area is then low enough for the spectral information from the studied point to be found.

The detectors (cameras) of today are, however, only two dimensional and three dimensions—two spatial and one spectral—are of interest. The third dimension must also be collected in some way. This could for instance be made by:

- A line scanning system, where one spectral and one spatial dimension are collected and the second spatial dimension is scanned, i.e. creating a push broom spectrometer.
- A spectral scanning system, where the collecting area are imaged on a detector chip giving the two spatial dimensions and the spectral information is detected by scanning through the wavelengths of interest with a very narrow spectral filter in front of the camera, i.e. creating a staring filtered camera.
- A system comprising a coded aperture (mask) combined with Compressed Sensing (CS), where both the spectral dimension and the two spatial dimensions are collected at once on the sensor. In this method the signal is multiplexed on the sensor and the images therefore have to be after-treated in order to resolve the information, i.e. creating a snap shot imager.

Bellow follows a description of the different systems.

A Line Scanning System

A line scanning imaging Raman system has the general layout of FIG. 1, but with a slit as input aperture 103. Particularly you can look at the description regarding a SORS system. In the same way the slit of the spectrometer is imaged on the detection zone 101 but here the illuminating laser radiation is evenly distributed over the whole detection zone, as a line overlapping the slit image. The number of spatial points on the target can here be at most as many as the number of pixels on the detector in that direction, typical in the order of one thousand. By scanning the line over the target area and taking multiple measurements the whole surface can be measured The drawback with such a system is that the line will have to be very thin, in the order of a few hundred micrometres, to be sensitive enough to detect single trace particles. This makes it unpractical to measure a larger surface since very many scans of the line need to be made to cover the surface and also the target must be more or less completely immobile during the detection time to be able to scan the surface in a controlled manner.

A Spectral Scanning System

If both directions of the 2-d detector area are used for spatial information, the spectral information must be recorded using spectral filters. In this case the detection area is imaged onto the detector chip without any aperture 103 or spectral device 104. Instead these parts are exchanged for a tunable narrow bandwidth filter. With the help of such narrow bandwidth filters a number of images may be recorded with a small spectral range in each image. The selection of a wavelength may be made by means of a narrow bandwidth tunable filter, e.g. a liquid crystal filter or an acuosto-optic filter. By choosing several wavelengths of interest you get a spectral image of the target. The spectral bands will be much fewer than with the push broom spectrometer and this will limit the number of substances that can be detected.

Further, since only a fraction of the collected light is passed through the filter, photons are lost and the target must be illuminated for a long time. Besides other inconveniences, there is a risk that the laser light may deteriorate the target, which could be a valuable personal property.

A Coded Aperture Combined with Compressed Sensing

An imaging system for Raman spectroscopy that uses a coded aperture has the general layout of FIG. 1. It can be seen as a spectrometer where the slit is exchanged for a coded aperture (or mask) 106-108 in FIG. 2, in the position of 103 in FIG. 1. The mask consists of sub-surfaces that either block or transmit radiation. In each measurement the spectral information is multiplexed with the spatial information. The information that is collected is sparse but can be recreated by choosing an appropriate algorithm and thereby both the spectral and spatial information of the detection zone can be measured at one single measurement.

Moreover, in order to increase the spatial or spectral information several images of the scene with different masks can be recorded, provided that the mask can be changed between the images. One way of doing this is to use a Digital Mirror Device (DMD).

THE PRESENT INVENTION

The basic principle of the invention is that by choosing a programmable coded aperture it will be possible to re-configure the aperture in such a way that the spectrometer may be ideally suitable for all the measurements and scenarios that have been discussed before.

The present invention has the general layout of FIG. 1. 101 denotes the target that is illuminated by laser radiation. The system comprises a focusable, imaging optical system (telescope or lenses) 102 that collects the Raman scattered light onto the programmable coded aperture 103, which is the entrance aperture of an imaging spectrometer comprising a dispersive device 104 and a 2-d detector 105.

The coded aperture could for instance be a digital mirror device (DMD) so that the mask can be chosen arbitrary. A DMD is made of millions of small mirrors that can be tilted to an "OFF" or "ON" state representing blocking and transmitting light trough the DMD.

By using a focusable imaging system 102 the light incident on the aperture 103 can either be focused onto it, completely defocused or everything in between. In this way the system can easily be adopted to different scenarios and applications, i.e. focused for 0-d and 1-d systems and unfocused for 2.d systems.

By means of this programmable coded aperture it is possible to choose the optimal entrance aperture of the spectrometer for each measurement and thereby the system can be reconfigured to optimally fit the specific target. When one looks for explosives of bulk quantities, or in gas phase, and thereby the spatial resolution is not vital, i.e. 0-d, the aperture could preferably be set as e.g. a Hadamard pattern 108 in FIG. 2 which maximizes the throughput of the spectrometer. Compared to a conventional slit-spectrograph the sheer increase in size of the aperture makes a coded aperture spectrograph much more sensitive. Also, compared to a fibre bundle solution, as discussed above, a coded aperture spectrometer does not suffer from the transmission losses in the fibre, which can be quite substantial if UV-light is used.

For identifying substances in semi-opaque containers using SORS, the system can be used in two different modes. A first mode when the aperture is formed as a slit 106 in FIG. 2 as explained in the SORS description above, i.e. the spectrometer functions as a conventional slit spectrometer (1-d), and a second mode when the aperture is set to a pre-defined mask for imaging purposes 107 (2-d), e.g. random open and closed pixels, to collect the circularly or elliptically distributed scattered light, as described above. In the latter case compressed sensing algorithms must be used to recreate the spectrum at different depths. One advantage with a larger aperture is a gain in sensitivity.

In a slit mode (1-d) the spectrometer can also be used as a line-scanning device, which can be useful in certain applications, e.g. if an imaging line scanning device is preferred. Since the line can be moved across a DMD, the line scanning can be made without moving the spectrometer.

Figure 2:
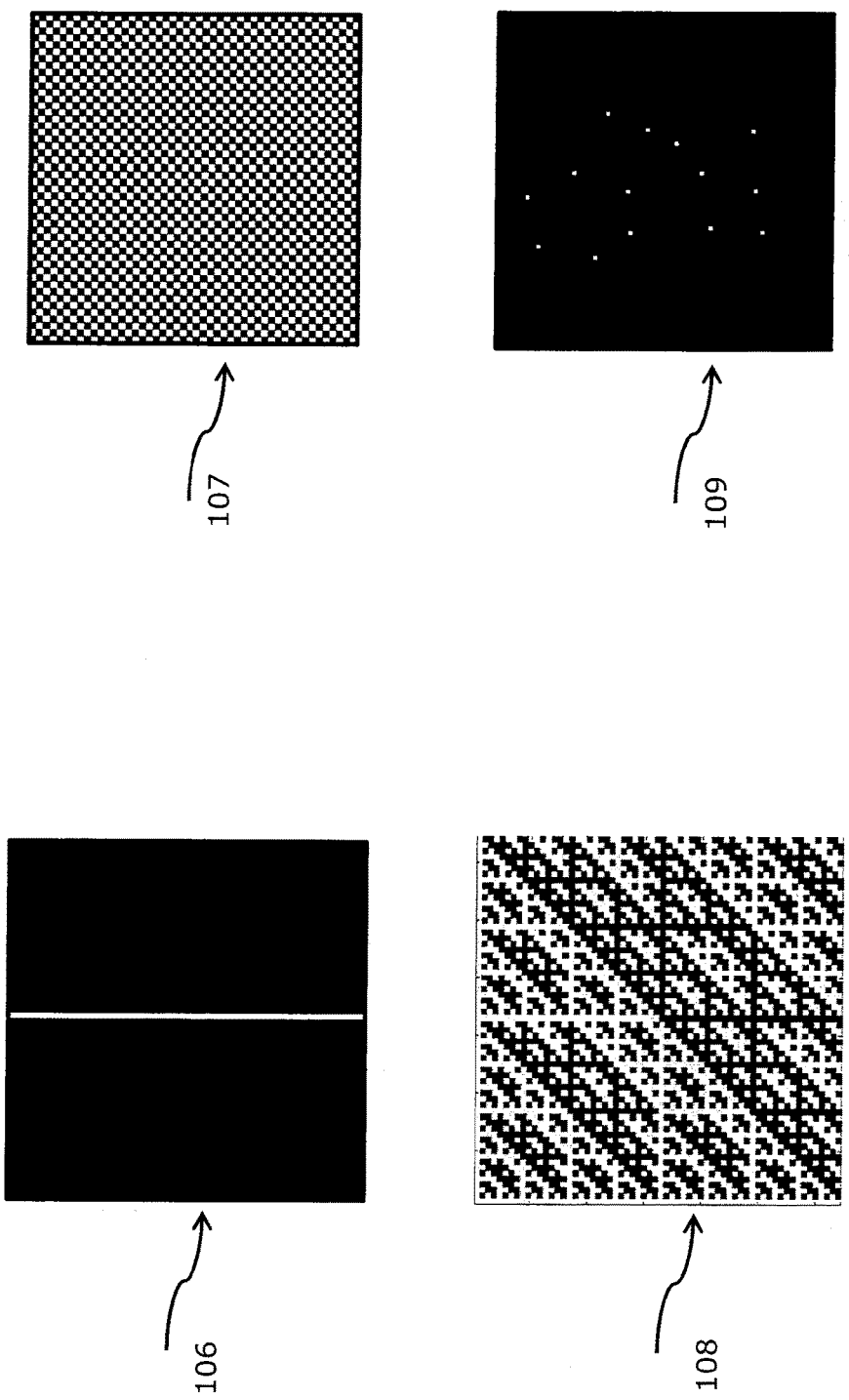
FIG. 2 shows different apertures that can be chosen on a DMD in an embodiment of the invention having the general layout of FIG. 1.

The slit 106 can also be broken up into several shorter slits or points (1-d) 109 in FIG. 2 and thereby lines or points on the target corresponding to said shorter lines or points may be examined with full spatial resolution (here called semi slit mode).

When you want to detect single particles on a surface, the aperture could preferably be put in pre-defined patterns for imaging purposes 107 in FIG. 2 and thereby the spectral and spatial information will be multiplexed on the sensor and compressed sensing algorithms can be used to achieve the spatial and spectral information of the target surface. Depending on the aperture and the number of images that are captured, the level of the spectral and spatial resolution of the target can be adapted the specific situation.

If the system finds a suspicious possible target in this mode (2-d) and the location of the target is well known but the spectral resolution is inadequate, the system can adept itself to use the semi slit mode (1-d) where the aperture is set to "ON"-state only in these locations and thereby full spectral resolution can be achieved there for better identification.

The system may also comprise a control and analysis device that chooses the initial measuring mode according to pre-defined criteria, analyses the measuring result and based on pre-defined decision criteria decides if the measuring mode should be changed and, if so, which mode to adopt. An operator of the system may of course also manually change between different measuring modes in a measuring sequence.

Moreover, since the programmable aperture can be chosen arbitrary it is easy to upgrade the system to new algorithms and applications.

In sum, a combined use of a programmable aperture and imaging Raman spectroscopy makes it possible for the detection equipment to quickly and easily adapt to be configured to be ideally suitable for measuring bulk substances, gas molecules from substances, substances in semi-opaque containers and even very small trace particles.

Compressed Sensing

Conventional measurements are limited by the Shannon theorem that states that the sampling rate must be at least twice the frequency of the signal. However using compressed sensing (CS) it is possible to measure a signal with far less measurements than normally. CS rely on most natural signal being sparse in some sense, i.e. a signal $S \in R^n$ that is expressed in an orthonormal basis $\Psi = [\psi_1, \psi_2, \psi_3 \ldots \psi_n]$ as $$S = \Sigma_{i=1}^n \langle S, \psi_i \rangle \psi_i$$

has several of the coefficients $\langle S, \psi_i \langle$ small enough to be discarded without any significant loss in the signal.

In a sense, CS is the same as data compression, but instead of doing it after the measurement, as a camera recording an image and then compressing the image, the compression in CS is made directly during the measurement. After the measurement the signal is restored using a mathematical algorithm.

When used together with imaging Raman spectroscopy it would mean that it is possible to measure not only two spatial dimensions but also the spectral dimension at the same time, thereby reducing acquisition time and also making it possible to measure on moving targets.

As stated above, FIG. 1 in connection with 107-108 in FIG. 2 show two coded apertures at the focal plane of an imaging spectrometer. To make a mathematical model of the system, let us for simplicity assume perfect optics and let $S_0(x,y;\lambda)$ be the spectral density function of the target that illuminates the input aperture $A(x,y)$. Then the transmitted spectral density directly after the aperture can be expressed by $$S_1(x,y;\lambda) = A(x,y)S_0(x,y;\lambda).$$

For a spectrometer with unit magnification, linear dispersion $\alpha$ in the x-direction and center wavelength $\lambda_c$ for an aperture at x=0 the spectral density just before the detector can be expressed by $$S_2(x,y;\lambda) = \iint \delta(x'-[x+\alpha(\lambda-\lambda_c)])\delta(y'-y)S_1(x',y';\lambda)dx'dy' = \iint \delta(x'-[x+\alpha(\lambda-\lambda_c)])(\delta(y'-y)A(x',y')S_0(x',y';\lambda)dx'dy'$$

where $\delta$ is the Dirac delta function.

Since the detector is insensitive to different wavelengths it can only measure the intensity of radiation rather than the spectral density, then the total radiation intensity on the detector can be written as $$D(x,y) = \int S_2(x,y;\lambda)d\lambda = \iiint \delta(x'-[x+\alpha(\lambda-\lambda_c)])\delta(y'-y)A(x',y')S_0(x',y';\lambda)dx'dy'd\lambda = \int A(x+\alpha(\lambda-\lambda_c),y)S_0(x+\alpha(\lambda-\lambda_c),y;\lambda)d\lambda.$$

The radiation intensity on pixel (i,j) on the detector can be described as $$D_{ij} = \iint P_{ij}(x,y)D(x,y)dxdy + N_{ij},$$

where $P_{ij}(x,y)$ is the characteristic function of pixel (i,j) and $N_{ij}$ is the noise factor.

Assume the pixels on the detector array are equal and square with the length of the side $\Delta_D$, then the function of the (i,j) pixel can be written as $$P_{ij}(x,y) = rect\left(\frac{x}{\Delta_D} - i, \frac{y}{\Delta_D} - j\right).$$

Then the measurement on pixel (i,j) on the detector is $$D_{ij} = \iint rect\left(\frac{x}{\Delta_D} - i, \frac{y}{\Delta_D} - j\right)D(x,y)dxdy + N_{ij} = \iiint rect\left(\frac{x}{\Delta_D} - i, \frac{y}{\Delta_D} - j\right)A(x+\alpha(\lambda-\lambda_c),y)S_0(x+\alpha(\lambda-\lambda_c),y;\lambda)dxdyd\lambda + N_{ij}.$$

Assume that the coded aperture has pinholes than are square and equal in size $\Delta_A$ and $T_{i'j'}$ represents the transmission pattern through the aperture at position (i',j'), i.e. on or off state. Then the aperture can be expressed as $$A(x,y) = \sum_{i',j'} rect\left(\frac{x}{\Delta_A} - i', \frac{y}{\Delta_A\Delta} - j'\right)T_{i'j'}$$

and thereby the measurement on the detector can be written as $$D_{ij} = \iiint rect\left(\frac{x}{\Delta_D} - i, \frac{y}{\Delta_D} - j\right)\sum_{i',j'} rect\left(\frac{x+\alpha(\lambda-\lambda_c)}{\Delta_A} - i', \frac{y}{\Delta_A} - j'\right)T_{i'j'} \times S_0(x+\alpha(\lambda-\lambda_c),y;\lambda)dxdyd\lambda + N_{ij}.$$

By writing the spectral density incident on the aperture in its discrete form $S_{lmk}$ the detector measurement can in matrix form be written as $$D_{ij} = \Sigma_k S_{(i+k)jk}T_{j(i+k)}N_{ij} = (PS)_{ij}N_{ij},$$

where P represent the propagation function through the system.

In matrix notation this can be written as $$d = HQ\theta$$

where H is the system transmission function.

A reconstruction for the data cube can be achieved from $$\hat{s} = Q\left\{\underset{\theta'}{argmin}\left\|\hat{d} - HQ\theta'\right\|_2^2 + \tau\|\theta'\|_1\right\}$$

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A stand-off optical measuring system based on Raman scattering for detecting and identifying chemical threat substances in a measuring zone, said system comprising: a spectrometer that includes a dispersive device in front of a 2-dimensional detector, the entrance of the spectrometer being a coded aperture that in each aperture point either transmits radiation towards the dispersive device or blocks the radiation from reaching the dispersive device, further including focusing optics imaging, focused or unfocused, radiation from the measuring zone onto the coded aperture, and a pulsed laser illuminating the measuring zone, the measuring system being configured to be able to quickly adapt to different measuring conditions by the coded aperture being a programmable coded aperture, which is at least able to adopt the following modes for the following cases:

When spatial resolution is not vital, such as in a point measurement, the programmable coded aperture is set as a pattern that maximizes the throughput of the spectrometer, such as a Hadamard pattern, When identifying substances in semi-opaque containers using SORS, the system is used in either of two different modes, a first mode in which the aperture is formed as a slit and the spectrometer functions as a conventional slit spectrometer, or a second mode in which the aperture is set to a pre-defined mask for imaging purposes that collects the circularly or elliptically distributed scattered light with spectral and spatial information multiplexed, and in which a calculation device using a compressed sensing algorithm recreates the spectrum at different depths, When in an imaging line scanning mode, the aperture is formed as a slit that is scanned over the aperture, or as an alternative, in a denominated semi slit mode, said slit may be broken up into several shorter slits or points and thereby lines or points on the target corresponding to said shorter lines or points may be examined with full spatial resolution, and When detecting single particles on a surface, the aperture is set to a pre-defined mask for imaging purposes, and the spectral and spatial information is multiplexed on the sensor, and a calculation device using a compressed sensing algorithm recreates the spatial and spectral information of the target surface.

2. The measuring system according to claim 1, further comprising a control and analysis device that chooses the initial measuring mode according to pre-defined criteria, analyzes the measuring result, and based on pre-defined decision criteria, decides if the measuring mode should be changed and, if so, which mode to adopt.

3. The measuring system according to claim 2, wherein the control and analysis device, when searching for single particles on a surface, as a first measuring mode chooses an imaging mode, analyzes the measuring results, and in case the analysis shows the location of a suspicious possible target, but the spectral resolution is inadequate, changes to the semi slit mode.

* * * * *